(12) United States Patent
Miyazono

(10) Patent No.: US 11,265,515 B2
(45) Date of Patent: Mar. 1, 2022

(54) WIRELESS COMMUNICATION APPARATUS, CAPSULE ENDOSCOPE SYSTEM, AND JUDGMENT METHOD

(71) Applicant: OLYMPUS CORPORATION, Tokyo (JP)

(72) Inventor: Toru Miyazono, Tama (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 16/951,462

(22) Filed: Nov. 18, 2020

(65) Prior Publication Data

US 2021/0092328 A1 Mar. 25, 2021

Related U.S. Application Data

(63) Continuation of application No. PCT/JP2019/007369, filed on Feb. 26, 2019.

(30) Foreign Application Priority Data

May 21, 2018 (JP) .............................. JP2018-096956

(51) Int. Cl.
*H04W 24/08* (2009.01)
*H04N 7/18* (2006.01)
(Continued)

(52) U.S. Cl.
CPC ......... *H04N 7/183* (2013.01); *A61B 1/00016* (2013.01); *A61B 1/041* (2013.01); *H04W 24/08* (2013.01)

(58) Field of Classification Search
CPC .... H04N 7/183; A61B 1/00016; A61B 1/041; H04W 24/08
See application file for complete search history.

(56) References Cited

U.S. PATENT DOCUMENTS

| 5,600,673 A | 2/1997 | Kimura et al. |
| 2011/0181273 A1* | 7/2011 | Iida ........................ A61B 5/062 324/207.11 |

(Continued)

FOREIGN PATENT DOCUMENTS

| JP | 63-061535 A | 3/1988 |
| JP | 08-163187 A | 6/1996 |

(Continued)

OTHER PUBLICATIONS

International Search Report dated Apr. 23, 2019 received in PCT/JP2019/007369.

*Primary Examiner* — Thai Q Tran
*Assistant Examiner* — Jose M Mesa
(74) *Attorney, Agent, or Firm* — Scully, Scott, Murphy & Presser, P.C.

(57) ABSTRACT

A wireless communication apparatus includes a phase detecting unit configured to detect a signal change point at which a signal decoded from a received wireless signal changes and detect a temporal position of the signal change point within one cycle defined by setting of a symbol rate as a phase, a vector generating unit configured to generate a vector which corresponds to the detected phase and which has a predetermined magnitude, a vector synthesizing unit configured to synthesize the generated vector in plurality to generate a synthesized vector, a calculating unit configured to calculate a parameter having a correspondence relationship with a magnitude of the generated synthesized vector, and a judging unit configured to judge whether or not a wireless signal is a specific wireless signal based on the calculated parameter.

12 Claims, 13 Drawing Sheets

(51) Int. Cl.
*A61B 1/00* (2006.01)
*A61B 1/04* (2006.01)

(56) References Cited

U.S. PATENT DOCUMENTS

2017/0305282 A1* 10/2017 Obayashi ................ H02J 50/12
2018/0295581 A1* 10/2018 Krishnamoorthy ... H04W 76/28

FOREIGN PATENT DOCUMENTS

| JP | 2005-318381 A | 11/2005 |
| JP | 2010-004144 A | 1/2010 |
| WO | 2012-169513 A1 | 12/2012 |

\* cited by examiner

WIRELESS COMMUNICATION APPARATUS, CAPSULE ENDOSCOPE SYSTEM, AND JUDGMENT METHOD

CROSS REFERENCE TO RELATED APPLICATION

This application is a continuation application of PCT/JP2019/007369 filed on Feb. 26, 2019 and claims benefit of Japanese Application No. 2018-096956 filed in Japan on May 21, 2018, the entire contents of which are incorporated herein by this reference.

BACKGROUND OF THE INVENTION

1. Field of the Invention

The present invention relates to a wireless communication apparatus which is capable of specifying a wireless signal, a capsule endoscope system, and a judgment method.

2. Description of the Related Art

Typically, in a medical field, an endoscope is used for observation, and the like, inside a living body. Further, in recent years, a capsule endoscope which is introduced inside a body by being swallowed by an examinee has been proposed as one type of endoscope. A capsule endoscope picks up images of objects inside a body cavity while moving inside a body in association with peristaltic activity, generates image data, encodes the image data in accordance with a predetermined rule to generate a wireless signal and transmits the wireless signal to an external receiving apparatus through wireless communication.

A capsule endoscope is driven by a built-in battery. Typically, at the capsule endoscope, to reduce power consumption of the battery, a wireless signal is intermittently transmitted or a symbol rate is changed in accordance with a state of a communication environment and a data amount of image data. The receiving apparatus therefore requires to detect presence of a wireless signal or detect a symbol rate of the wireless signal.

A signal obtained by decoding the encoded wireless signal periodically changes in accordance with the symbol rate. Temporal positions of signal change points at which the decoded signal changes can be expressed with phases. Analysis of the phases of the signal change points is typically used as means for analyzing the received wireless signal.

The phase can be expressed using, for example, a vector. Japanese Patent Application Laid-Open Publication No. 2005-318381 discloses a zero cross detection circuit which obtains a phase center using a vector.

SUMMARY OF THE INVENTION

A wireless communication apparatus according to one aspect of the present invention is a wireless communication apparatus including a processor, the processor being configured to detect a signal change point at which a signal decoded from a received wireless signal changes, and detect a temporal position of the signal change point within one cycle defined by a predetermined symbol rate as a phase, generate a vector which corresponds to the phase and which has a predetermined magnitude, synthesize the vector in plurality to generate a synthesized vector, calculate a parameter having a correspondence relationship with a magnitude of the synthesized vector, and judge whether or not the received wireless signal is a wireless signal from a predetermined transmission apparatus based on the parameter.

A wireless communication apparatus according to another aspect of the present invention is a wireless communication apparatus including a processor configured to perform a plurality of kinds of computation processing, the processor being configured to, for each of the plurality of kinds of computation processing: detect a signal change point at which a signal decoded from a received wireless signal changes, and detect a temporal position of the signal change point within one cycle defined by a predetermined symbol rate as a phase; generate a vector which corresponds to the phase and which has a predetermined magnitude; synthesize the vector in plurality to generate a synthesized vector, and calculate a parameter having a correspondence relationship with a magnitude of the synthesized vector, for each of the plurality of kinds of computation processing. The symbol rate is different for each of the plurality of kinds of computation processing, and the processor is further configured to judge a symbol rate of the wireless signal based on the parameter in plurality calculated through the plurality of kinds of computation processing.

A capsule endoscope system according to one aspect of the present invention includes a capsule endoscope which picks up an image inside a subject to generate image data and transmits the image data using a wireless signal, and a wireless communication apparatus.

A judgment method according to one aspect of the present invention includes detecting a signal change point at which a signal decoded from a received wireless signal changes and detecting a temporal position of the signal change point within one cycle defined by a predetermined symbol rate as a phase, generating a vector which corresponds to the phase and which has a predetermined magnitude, synthesizing the vector in plurality to generate a synthesized vector, calculating a parameter having a correspondence relationship with a magnitude of the synthesized vector, and judging whether or not the received wireless signal is a wireless signal from a predetermined transmission apparatus based on the parameter.

DETAILED DESCRIPTION OF THE PREFERRED EMBODIMENTS

Embodiments of the present invention will be described below with reference to the drawings.

First Embodiment (Configuration of Endoscope System)

Figure 1:
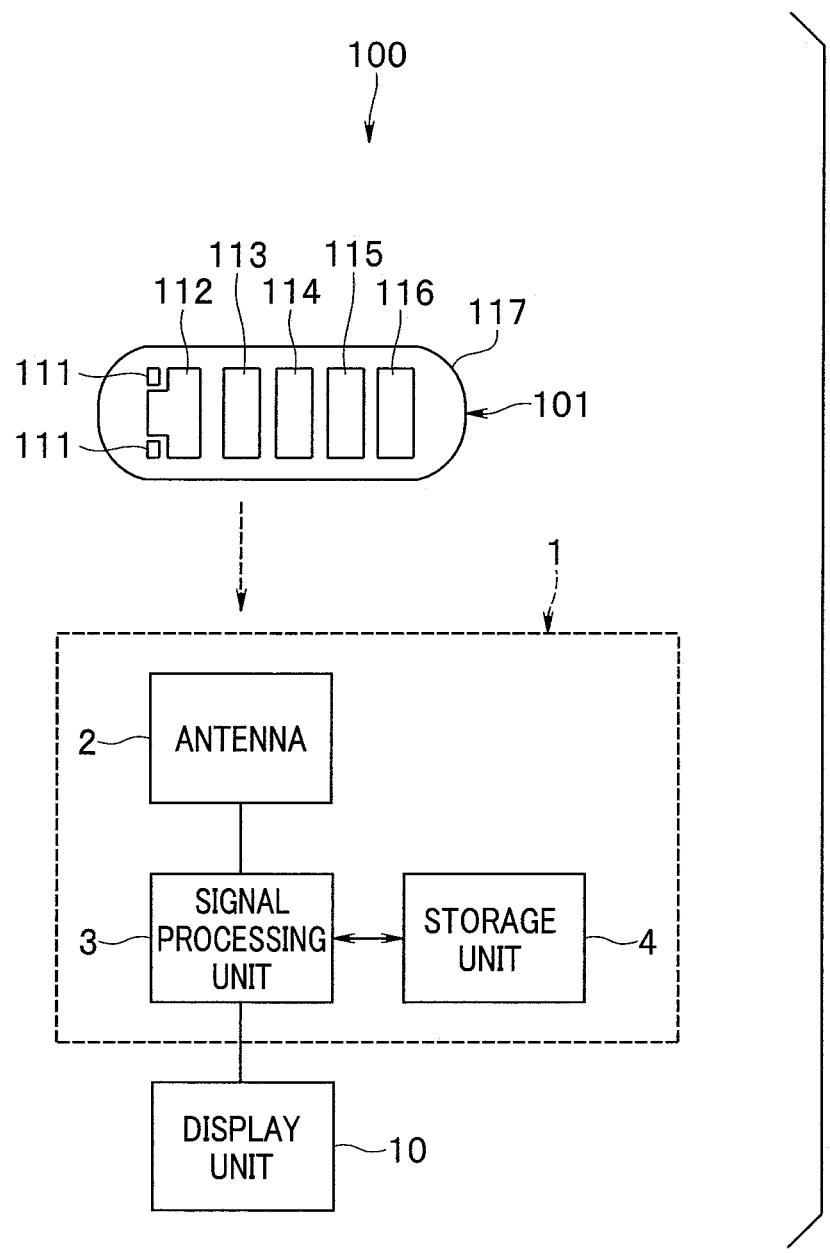
FIG. 1 is an explanatory diagram illustrating a capsule endoscope system according to a first embodiment of the present invention.

A configuration of a capsule endoscope system according to a first embodiment of the present invention will be described first. FIG. 1 is an explanatory diagram illustrating a configuration of the capsule endoscope system according to the present embodiment. As illustrated in FIG. 1, a capsule endoscope system 100 includes a capsule endoscope 101 and a wireless communication apparatus 1 according to the present embodiment.

The capsule endoscope 101 has a dimension and a shape which allow the capsule endoscope to be disposed within a body cavity of an examinee and is introduced into a cavity of a digestive system by being swallowed by the examinee. Further, the capsule endoscope 101 is configured to be able to pick up an image inside the subject to generate image data and transmit the image data using a wireless signal. In the present embodiment, the capsule endoscope 101 includes an illuminating unit 111, an image pickup unit 112, a wireless communication unit 113, a storage unit 114, a power supply unit 115, a control unit 116, and a chassis 117. The chassis 117 has a shape of an elongated capsule. Components of the capsule endoscope 101 other than the chassis 117 are sealed inside the chassis 117.

The illuminating unit 111, which includes a light emitting device such as an LED, generates illumination light for illuminating an object inside the subject. The image pickup unit 112, which includes an image pickup device such as a CCD, picks up an image of the object illuminated by the illuminating unit 111 to generate image data.

The wireless communication unit 113, which includes an encoding modulating unit and an antenna, transmits an encoded wireless signal in accordance with a predetermined rule. FIG. 1 indicates a wireless signal with a dashed arrow. The wireless signal includes a preamble located at a head portion, and main data subsequent to the preamble. In the present embodiment, the main data is the image data generated by the image pickup unit 112.

Note that the wireless communication unit 113 may have a function of receiving a wireless signal transmitted by the wireless communication apparatus 1 as well as the function of transmitting a wireless signal. In this case, the wireless communication unit 113 includes a demodulating unit which restores information from the received wireless signal.

The storage unit 114, which includes a memory such as a RAM, is configured to be able to store the image data generated by the image pickup unit 112. The power supply unit 115, which includes, for example, a battery, is configured to be able to supply drive power to the respective units of the capsule endoscope 101. The control unit 116 controls operation of the respective units of the capsule endoscope 101.

The wireless communication apparatus 1 is physically separate from the capsule endoscope 101. Note that the wireless communication apparatus 1 may be, for example, part of a stationary apparatus such as a work station or may be part of a portable terminal apparatus which is driven by a battery.

In the present embodiment, the wireless communication apparatus 1 includes an antenna 2, a signal processing unit 3 and a storage unit 4. The antenna 2 receives a wireless signal transmitted by the wireless communication unit 113 of the capsule endoscope 101. The signal processing unit 3 performs predetermined processing on the received wireless signal. The predetermined processing includes processing of acquiring image data included in the wireless signal. A configuration of the signal processing unit 3 will be described in detail later.

The storage unit 4 can store the acquired image data, a detection result of a signal detecting unit which will be described later, and setting of a symbol rate. The storage unit 4 may include a volatile memory such as a RAM or may include a rewritable non-volatile memory such as a flash memory and a magnetic disk apparatus.

The capsule endoscope system 100 may further include a display unit 10. The display unit 10 may include, for example, a display apparatus such as an LCD. The display unit 10 displays an image corresponding to the image data acquired by the signal processing unit 3 of the wireless communication apparatus 1. FIG. 1 illustrates an example where the display unit 10 is directly connected to the wireless communication apparatus 1.

Figure 2:
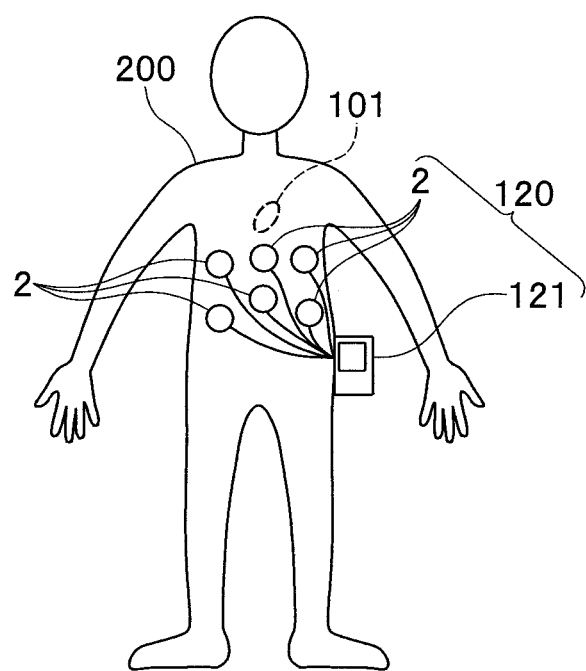
FIG. 2 is a schematic diagram illustrating an aspect of use of the capsule endoscope system according to the first embodiment of the present invention.

Here, an aspect of use of the capsule endoscope system 100 will be described using an example of a case where the wireless communication apparatus 1 is part of the portable terminal apparatus 120. FIG. 2 is a schematic diagram illustrating an aspect of use of the capsule endoscope system 100. While the capsule endoscope system 100 is used, the capsule endoscope 101 is disposed inside a body cavity of an examinee 200.

The portable terminal apparatus 120 includes the wireless communication apparatus 1, a body portion 121 and a battery which is not illustrated. Components of the wireless communication apparatus 1 other than the antenna 2 are accommodated in the body portion 121. The battery which is not illustrated is mounted on the body portion 121. While the capsule endoscope system 100 is used, the body portion 121 is attached to outside of the body of the examinee 200.

In an example illustrated in FIG. 2, a plurality of the antennas 2 are provided. Each of the plurality of antennas 2 is connected to the body portion 121 through signal lines. While the capsule endoscope system 100 is used, the plurality of antennas 2 are disposed on a body surface of the examinee 200.

(Configuration of Signal Processing Unit)

Figure 3:
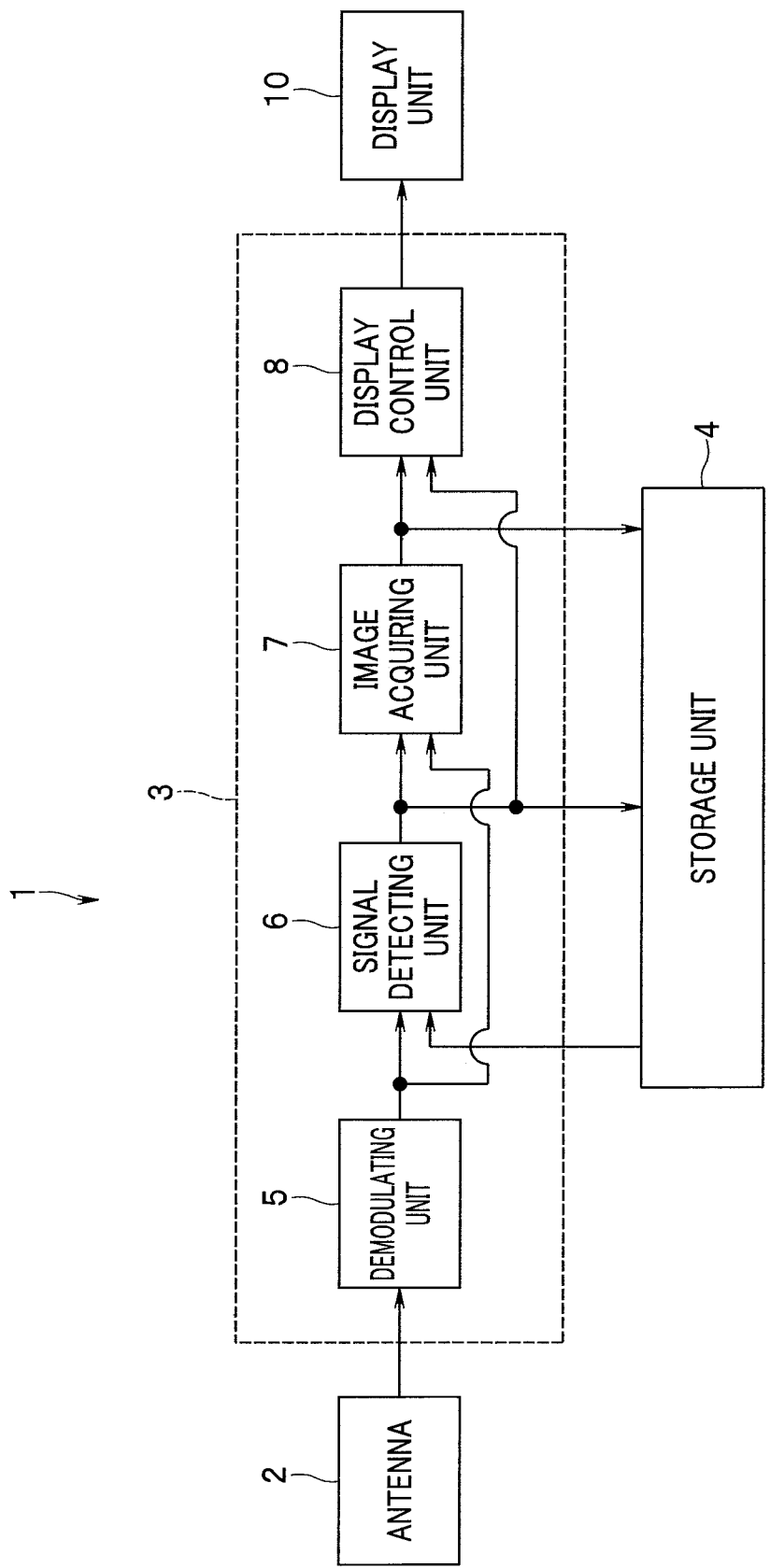
FIG. 3 is a functional block diagram illustrating a configuration of a wireless communication apparatus according to the first embodiment of the present invention.

A configuration of the signal processing unit 3 will be described next with reference to FIG. 3. FIG. 3 is a functional block diagram illustrating the configuration of the wireless communication apparatus 1. As illustrated in FIG. 3, the signal processing unit 3 includes a demodulating unit 5, a signal detecting unit 6, an image acquiring unit 7, and a display control unit 8.

The demodulating unit 5 performs processing of restoring the wireless signal received at the antenna 2 to a signal in a form which can be processed at the signal detecting unit 6 and the image acquiring unit 7, and outputs the restored signal to the signal detecting unit 6 and the image acquiring unit 7. In the present embodiment, the wireless signal is restored as a signal encoded in accordance with a predetermined rule. In the following description, the signal restored by the demodulating unit 5 will also be referred to as a wireless signal for convenience sake.

The signal detecting unit 6 is configured to be able to detect predetermined information from the wireless signal received by the wireless communication apparatus 1 and output the detection result to the storage unit 4, the image acquiring unit 7 and the display control unit 8. The storage unit 4 stores the detection result of the signal detecting unit 6. The signal detecting unit 6 will be described in detail later.

The image acquiring unit 7 is configured to be able to acquire the image data generated by the image pickup unit 112 (see FIG. 1) of the capsule endoscope 101 from the wireless signal received by the wireless communication apparatus 1 and output the acquired image data to the storage unit 4 and the display control unit 8. The storage unit 4 stores the image data acquired by the image acquiring unit 7. In the present embodiment, the image acquiring unit 7 can acquire the image data based on the detection result of the signal detecting unit 6. Operation of the image acquiring unit 7 will be described later.

The display control unit 8 is configured to be able to output information regarding the detection result of the signal detecting unit 6 and the image data acquired by the image acquiring unit 7 to the display unit 10. Further, the display control unit 8 can control content to be outputted to the display unit 10 based on the detection result of the signal detecting unit 6. Operation of the display control unit 8 will be described later.

The signal processing unit 3 further includes a clock generating unit which is not illustrated. The clock generating unit which is not illustrated generates a processing clock at a predetermined frequency. The processing clock is inputted to a phase detecting unit which will be described later.

Note that in the present embodiment, the demodulating unit 5, the signal detecting unit 6, the image acquiring unit 7 and the display control unit 8 may be respectively constituted as different electronic circuits. Alternatively, at least part of the demodulating unit 5, the signal detecting unit 6, the image acquiring unit 7 and the display control unit 8 may be constituted as circuit blocks in an integrated circuit such as a field programmable gate array (FPGA). Alternatively, at least part of the demodulating unit 5, the signal detecting unit 6, the image acquiring unit 7 and the display control unit 8 may be constituted with processors including hardware. In other words, the signal processing unit 3 may include at least one central processing unit (hereinafter, referred to as a CPU), and the storage unit 4 may store programs which implement functions of at least part of the demodulating unit 5, the signal detecting unit 6, the image acquiring unit 7 and the display control unit 8. In this case, functions of at least part of the demodulating unit 5, the signal detecting unit 6, the image acquiring unit 7 and the display control unit 8 are implemented by the CPU reading out the programs from the storage unit 4 and executing the programs.

(Configuration of Signal Detecting Unit)

Figure 4:
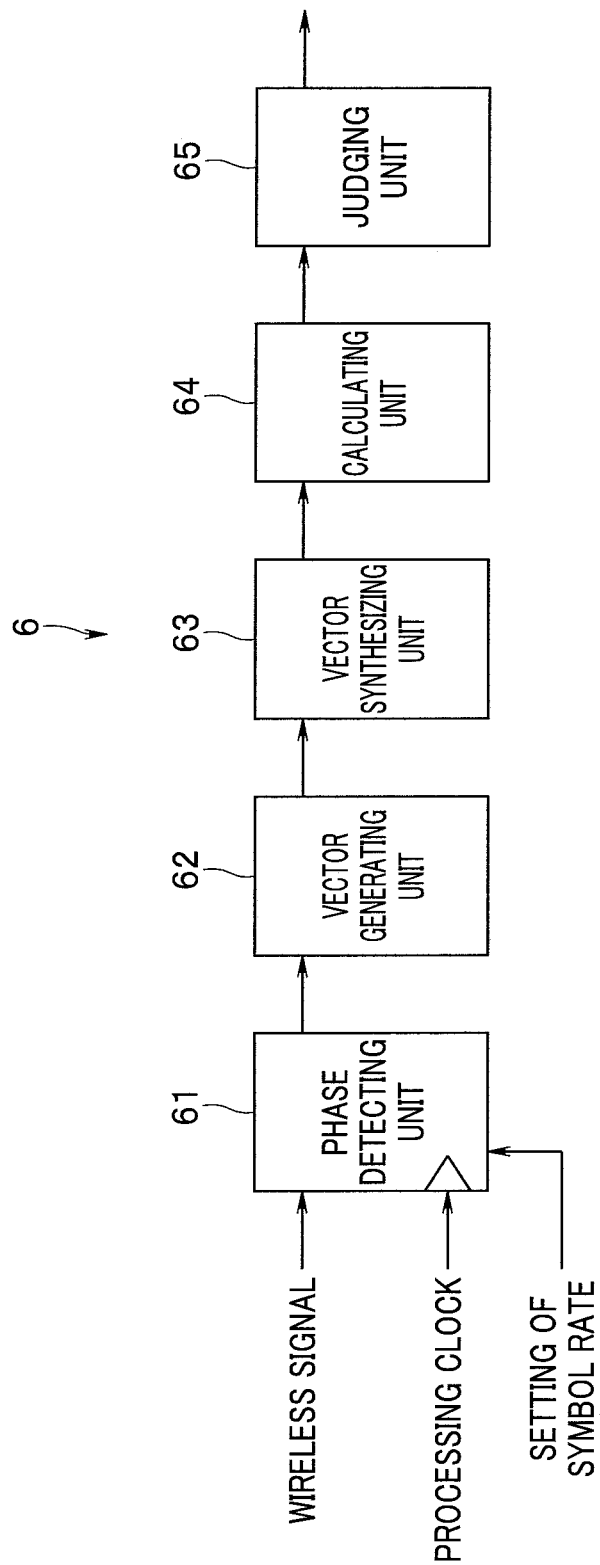
FIG. 4 is a functional block diagram illustrating a configuration of a signal detecting unit in the first embodiment of the present invention.

A configuration of the signal detecting unit 6 will be described next with reference to FIG. 4. FIG. 4 is a functional block diagram illustrating the configuration of the signal detecting unit 6. As illustrated in FIG. 4, the signal detecting unit 6 includes a phase detecting unit 61, a vector generating unit 62, a vector synthesizing unit 63, a calculating unit 64 and a judging unit 65 sequentially provided from a side closer to the demodulating unit 5 (see FIG. 3).

The phase detecting unit 61 receives input of a signal obtained by decoding the wireless signal restored by the demodulating unit 5 and the processing clock. Further, the phase detecting unit 61 is configured to be able to read out the setting of the symbol rate stored in the storage unit 4. Note that the setting of the symbol rate is a predetermined value of the symbol rate. In the present embodiment, the phase detecting unit 61 detects a temporal position at which the signal decoded from the wireless signal changes, detects a phase of the temporal position based on the setting of the symbol rate, and outputs the detected phase to the vector generating unit 62. The temporal position at which the decoded signal changes will be referred to as a signal change point.

Note that the decoded signal is, for example, a signal of one bit expressed with 0 and 1. Here, 0 refers to a low-level signal, and 1 refers to a high-level signal. In this case, a temporal position at which the signal changes from a low level to a high level or from a high level to a low level becomes the signal change point.

The vector generating unit 62 generates a vector which corresponds to the phase detected by the phase detecting unit 61 and which has a predetermined magnitude and outputs the generated vector to the vector synthesizing unit 63. The magnitude of the vector is, for example, 1.

The vector synthesizing unit 63 synthesizes a plurality of vectors generated by the vector generating unit 62 to generate a synthesized vector and outputs the generated synthesized vector to the calculating unit 64. In the present embodiment, the synthesized vector is generated by synthesizing a plurality of vectors generated based on a plurality of signal change points detected during a predetermined period by the phase detecting unit 61.

A series of processing at the phase detecting unit 61, the vector generating unit 62 and the vector synthesizing unit 63, that is, a method for generating a synthesized vector from a wireless signal will be described in further detail later.

The calculating unit 64 calculates a parameter having a correspondence relationship with a magnitude of the synthesized vector generated at the vector synthesizing unit 63 and outputs the calculated parameter to the judging unit 65. The parameter may be the magnitude of the synthesized vector itself. Alternatively, the parameter may be an average value of magnitudes of a plurality of vectors used to generate one synthesized vector. The average value of magnitudes of a plurality of vectors can be obtained by dividing the magnitude of the synthesized vector by the number of vectors, and thus has a correspondence relationship with the magnitude of the synthesized vector. Alternatively, the parameter may have a correspondence relationship with components on the real axis and components corresponding to the imaginary axis when the synthesized vector is expressed with a complex number.

The judging unit 65 judges whether or not the wireless signal is a specific wireless signal based on the parameter calculated by the calculating unit 64. In the present embodiment, particularly, the judging unit 65 judges whether the wireless signal is a specific wireless signal or noise by comparing the parameter with a predetermined threshold. In the present embodiment, the specific wireless signal is a wireless signal having a symbol rate which is the same or substantially the same as a symbol rate in the setting of the symbol rate inputted to the phase detecting unit 61. Particularly, in a case where the wireless communication unit 113 (see FIG. 1) of the capsule endoscope 101 transmits a wireless signal at a symbol rate which is the same as the symbol rate in the above-described setting of the symbol rate, the wireless signal is a wireless signal transmitted by the wireless communication unit 113 of the capsule endoscope 101.

Further, the judging unit 65 judges whether a reception condition of the specific wireless signal is good or bad by comparing the parameter calculated by the calculating unit 64 with a predetermined threshold. A judgment result as to whether or not the wireless signal is the specific wireless signal and a judgment result of the reception condition of the specific wireless signal correspond to information detected from the wireless signal. The judging unit 65 can output these judgement results to the storage unit 4, the image acquiring unit 7 and the display control unit 8 (see FIG. 3) as the detection result of the signal detecting unit 6.

(Method for Generating Synthesized Vector)

Figure 5:
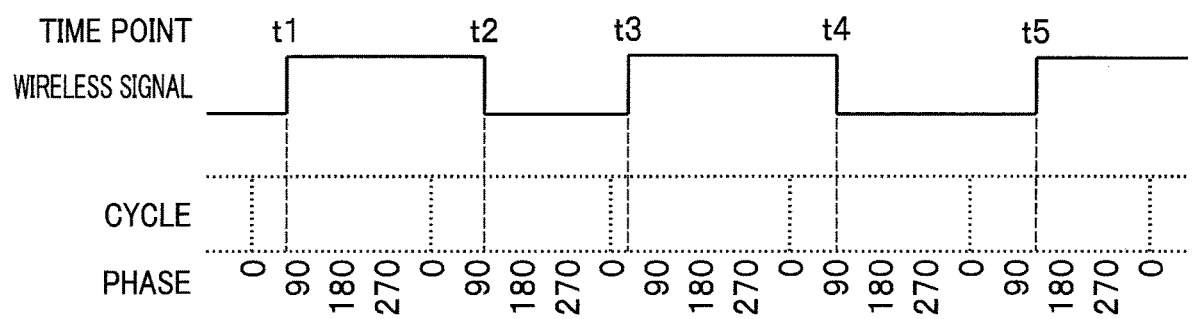
FIG. 5 is an explanatory diagram illustrating an example of a wireless signal and a phase in the first embodiment of the present invention.

A method for generating a synthesized vector from a wireless signal will be described in detail next. Here, description will be provided using an example of a case where five signal change points are detected during a predetermined period. First, a method for detecting a phase at the phase detecting unit 61 will be described with reference to FIG. 5. FIG. 5 is an explanatory diagram illustrating an example of a wireless signal and a phase. In the example illustrated in FIG. 5, the signal changes from a low level to a high level at each of time points t1, t3 and t5, and the signal changes from a high level to a low level at each of time points t2 and t4.

In FIG. 5, a plurality of sections drawn with dotted lines schematically indicate a plurality of cycles defined by setting of the symbol rate, and a length of one section corresponds to one cycle. Here, a period corresponding to five cycles is set as the predetermined period. Further, numbers provided below the plurality of sections indicate respective phases (°) of the plurality of cycles. In each of the plurality of cycles, a phase at a start point is 0°, and a phase at an end point is 360°. Note that an end point of an n-th (where n is an integer from 1 to 4) cycle matches a start point of an n+1-th cycle. FIG. 5 illustrates only a number indicating the phase at the start point, that is, 0 at the position of the end point for convenience sake.

Further, in FIG. 5, dashed lines extending from the signal change points indicate temporal positions of the signal change points. As illustrated in FIG. 5, a temporal position of arbitrary one signal change point can be expressed as a temporal position in arbitrary one cycle defined by the setting of the symbol rate, that is, a phase. The phase detecting unit 61 detects a temporal position of the signal change point within one cycle defined by the setting of the symbol rate as a phase.

Figure 6A:
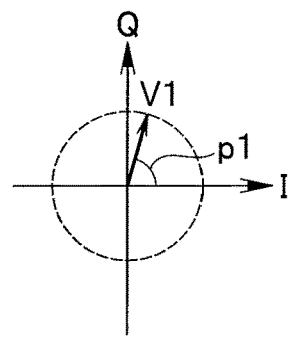
FIG. 6A is an explanatory diagram illustrating a vector generated from the phase illustrated in FIG. 5.
Figure 6B:
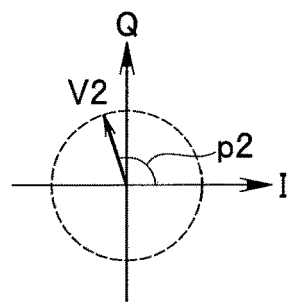
FIG. 6B is an explanatory diagram illustrating a vector generated from the phase illustrated in FIG. 5.
Figure 6C:
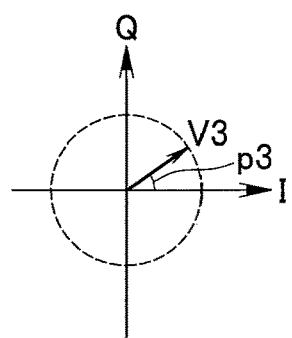
FIG. 6C is an explanatory diagram illustrating a vector generated from the phase illustrated in FIG. 5.
Figure 6D:
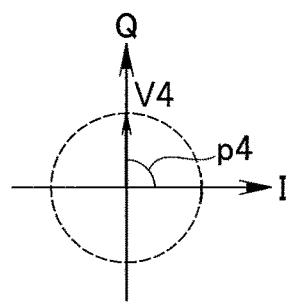
FIG. 6D is an explanatory diagram illustrating a vector generated from the phase illustrated in FIG. 5.
Figure 6E:
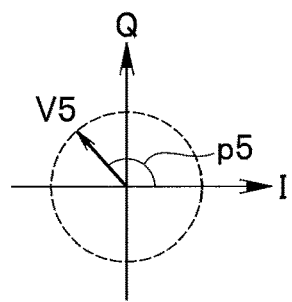
FIG. 6E is an explanatory diagram illustrating a vector generated from the phase illustrated in FIG. 5.

A method for generating a vector at the vector generating unit 62 will be described next with reference to FIG. 6 A to FIG. 6E. FIG. 6A to FIG. 6E are explanatory diagrams illustrating vectors generated from the phases illustrated in FIG. 5. FIG. 6A to FIG. 6E indicate the vectors with arrows. A length of the arrow indicates a magnitude of the vector. FIG. 6A illustrates a vector V1 generated from a phase p1 corresponding to the time point t1 in FIG. 5. FIG. 6B illustrates a vector V2 generated from a phase p2 corresponding to the time point t2 in FIG. 5. FIG. 6C illustrates a vector V3 generated from a phase p3 corresponding to the time point t3 in FIG. 5. FIG. 6D illustrates a vector V4 generated from a phase p4 corresponding to the time point t4 in FIG. 5. FIG. 6E illustrates a vector V5 generated from a phase p5 corresponding to the time point t5 in FIG. 5. Further, in FIG. 6A to FIG. 6E, an I axis corresponds to the real axis, and a Q axis corresponds to the imaginary axis.

The vector generating unit 62 generates a vector corresponding to the phase detected by the phase detecting unit 61 by setting, for example, the phase detected by the phase detecting unit 61 as an angle of the vector based on the real axis and setting a magnitude of the vector as 1. Note that in a case where the angle of the vector is set as $\theta$, and the magnitude of the vector is set as 1, a component of the vector on the real axis becomes $\cos \theta$ and a component of the vector on the imaginary axis becomes $\sin \theta$. In the present embodiment, the vector may be expressed with the component on the real axis and the component on the imaginary axis.

Figure 7:
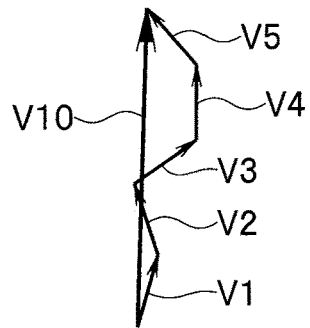
FIG. 7 is an explanatory diagram illustrating a synthesized vector generated by synthesizing the vectors illustrated in FIG. 6A to FIG. 6E.

A method for synthesizing vectors at the vector synthesizing unit 63 will be described next with reference to FIG. 7. FIG. 7 illustrates a synthesized vector V10 generated by synthesizing the vectors V1 to V5 illustrated in FIG. 6A to FIG. 6E. FIG. 7 indicates the respective vectors V1 to V5 and the synthesized vector V10 with arrows in a similar manner to FIG. 6A to FIG. 6E. Note that in FIG. 6A to FIG. 6E and FIG. 7, the vectors V1 to V5 are drawn with the arrows having the same length.

The vector synthesizing unit 63 synthesizes the vectors V1 to V5 generated by the vector generating unit 62 during a predetermined period to generate the synthesized vector V10. Specifically, for example, the vector synthesizing unit 63 calculates the synthesized vector V10 by calculating a component of the synthesized vector V10 on the real axis by adding respective components of the vectors V1 to V5 on the real axis, and calculating a component of the synthesized vector V10 on the imaginary axis by adding respective components of the vectors V1 to V5 on the imaginary axis.

Note that an example of a case where five signal change points are detected during the predetermined period has been described above. However, a length of the predetermined period may be arbitrarily, and the number of signal change points detected during the predetermined period may be arbitrary. Further, in a case where the period during which the signal change point is detected is fixed, the number of signal change points to be detected can vary in accordance with an aspect of the wireless signal. Therefore, in this case, the number of vectors to be used for generating the synthesized vector can vary.

(Judgment Method at Judging Unit)

A judgment method at the judging unit 65 will be described next. Here, an example of a case where the parameter calculated by the calculating unit 64 is the magnitude of the synthesized vector itself will be described. The calculating unit 64, for example, calculates the magnitude of the synthesized vector from the component of the synthesized vector on the real axis and the component of the synthesized vector on the imaginary axis.

The judging unit 65 judges whether or not the wireless signal is a specific wireless signal by comparing the magnitude of the synthesized vector with the predetermined threshold. For example, in a case where the magnitude of the synthesized vector is equal to or greater than the predetermined threshold, the judging unit 65 judges that the wireless signal is the specific wireless signal. As described above, in the present embodiment, the specific wireless signal is a wireless signal having a symbol rate which is the same or substantially the same as the symbol rate in the setting of the symbol rate inputted to the phase detecting unit 61.

On the other hand, in a case where the magnitude of the synthesized vector is less than the predetermined threshold, the judging unit 65 judges that the wireless signal is not the specific wireless signal. In the present embodiment, particularly, the judging unit 65 judges that the wireless signal is noise in a case where the magnitude of the synthesized vector is less than the predetermined threshold.

Figure 8:
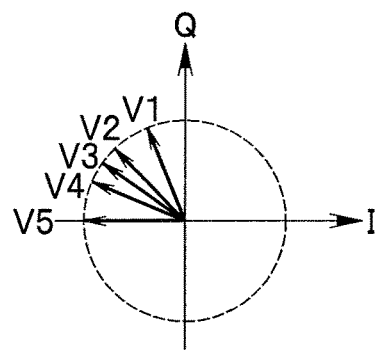
FIG. 8 is an explanatory diagram illustrating vectors generated based on signal change points detected from a specific wireless signal.
Figure 9:
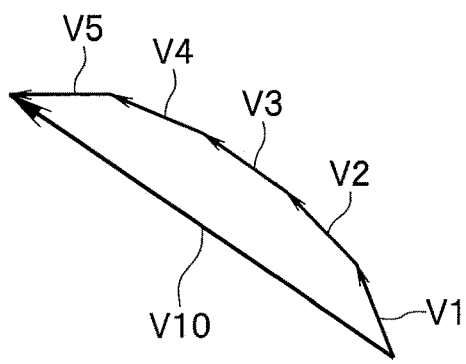
FIG. 9 is an explanatory diagram illustrating a synthesized vector generated by synthesizing the vectors illustrated in FIG. 8.
Figure 10:
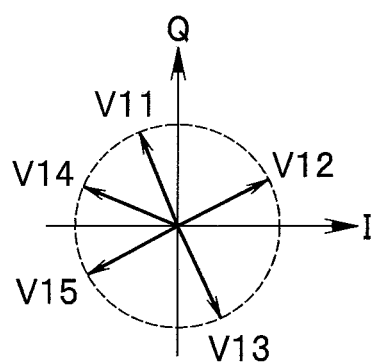
FIG. 10 is an explanatory diagram illustrating vectors generated based on signal change points detected from noise.
Figure 11:
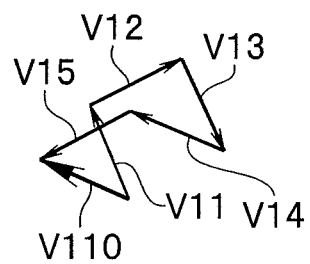
FIG. 11 is an explanatory diagram illustrating a synthesized vector generated by synthesizing the vectors illustrated in FIG. 10.

Reasons why whether the wireless signal is the specific wireless signal or noise can be judged in accordance with the magnitude of the synthesized vector will be described below with reference to FIG. 8 to FIG. 11. FIG. 8 illustrates the vectors V1, V2, V3, V4 and V5 generated based on the signal change points detected from the wireless signal corresponding to the specific wireless signal. Note that directions of the vectors V1 to V5 illustrated in FIG. 8 are made different from directions of the vectors V1 to V5 illustrated in FIG. 6A to FIG. 6E and FIG. 7 for convenience sake. FIG. 9 illustrates the synthesized vector V10 generated by synthesizing the vectors V1 to V5 illustrated in FIG. 8. FIG. 10 illustrates vectors V11, V12, V13, V14 and V15 generated based on the signal change points detected from the wireless signal corresponding to noise. FIG. 11 illustrates a synthesized vector V110 generated by synthesizing the vectors V11 to V15.

In FIG. 8 to FIG. 11, the vectors are indicated with arrows. A length of the arrow indicates a magnitude of the vector. It is assumed that magnitudes of the vectors V1 to V5 and V11 to V15 are the same. In FIG. 8 to FIG. 11, the vectors V1 to V5 and the vectors V11 to V15 are drawn with arrows having the same length.

As illustrated in FIG. 8, respective directions of the vectors V1 to V5 which are generated based on a plurality of signal change points detected from the wireless signal corresponding to the specific wireless signal match to some degree. This is because the specific wireless signal changes at a timing which is substantially the same as the setting of the symbol rate, and temporal positions of the signal change points within one cycle defined by the setting of the symbol rate are substantially the same among the plurality of signal change points, and, as a result, phases are substantially the same among the plurality of signal change points.

In contrast, as illustrated in FIG. 10, respective directions of the vectors V11 to V15 which are generated based on a plurality of signal change points detected from the wireless signal corresponding to noise become random. This is because a signal of noise randomly changes, and temporal positions of the signal change points of the plurality of signal change points within one cycle defined by the setting of the symbol rate randomly change, and, as a result, phases of the plurality of signal change points randomly change.

As a result of the directions of the vectors V11 to V15 being random in this manner, as illustrated in FIG. 9 and FIG. 11, a magnitude of the synthesized vector V110 generated by synthesizing the vectors V11 to V15 becomes smaller than a magnitude of the synthesized vector V10 generated by synthesizing the vectors V1 to V5. By utilizing such property that the magnitude of the synthesized vector generated from noise becomes smaller than the magnitude of the synthesized vector generated from the specific wireless signal, it is possible to judge whether the wireless signal is the specific wireless signal or noise.

An example of a case where the parameter calculated by the calculating unit 64 is the magnitude of the synthesized vector itself has been described above. As described above, in a case where a period during which the signal change points are detected is made fixed, the number of signal change points to be detected can vary in accordance with an aspect of the wireless signal. Thus, the parameter is preferably set while the number of signal change points to be detected is taken into account. Such a parameter includes an average value of magnitudes of a plurality of vectors used to generate one synthesized vector.

Further, the judging unit 65 can judge whether or not the wireless signal is the specific wireless signal as long as a parameter having a correspondence relationship with the magnitude of the synthesized vector is used, and is not limited to the magnitude of the synthesized vector itself and the average value. For example, the judging unit 65 may judge whether or not the wireless signal is the specific wireless signal by comparing the component of the synthesized vector on the real axis and the component of the synthesized vector on the imaginary axis with respective predetermined thresholds. In this case, the judging unit 65 may judge that the wireless signal is the specific wireless signal in a case where one of the component on the real axis and the component on the imaginary axis is equal to or greater than the predetermined threshold, or may judge that the wireless signal is the specific wireless signal in a case where both of the component on the real axis and the component on the imaginary axis are equal to or greater than the predetermined thresholds.

Further, in the present embodiment, the judging unit 65 judges whether a reception condition of the specific wireless signal is good or bad regardless of specification of the wireless signal as described above. In other words, the judging unit 65 judges whether the reception condition of the specific wireless signal is good or bad by comparing the parameter calculated by the calculating unit 64 with the predetermined threshold.

Note that the threshold to be used to judge whether the reception condition is good or bad (hereinafter, referred to as a second threshold) may be the same as or different from the threshold to be used to judge whether or not the wireless signal is the specific wireless signal (hereinafter, referred to as a first threshold). For example, in a case where a magnitude of the parameter calculated when directions of the plurality of vectors are completely the same is set at 100%, the first threshold may be set at 20%, and the second threshold may be set at 60%. In this case, the judging unit 65 first judges whether or not the wireless signal is the specific wireless signal by comparing the parameter with the first threshold. In a case where the parameter is less than the first threshold (20%), the judging unit 65 judges that the received wireless signal is not the specific wireless signal.

In a case where the parameter is equal to or greater than the first threshold, the judging unit 65 judges that the received wireless signal is the specific wireless signal. In this case, the judging unit 65 then judges whether or not the reception condition is good or bad by comparing the parameter with the second threshold. In a case where the parameter is equal to or greater than the second threshold (60%), the judging unit 65 judges that the reception condition is good. On the other hand, in a case where the parameter is less than the second threshold, the judging unit 65 judges that the reception condition is bad. Examples of a case where the parameter is less than the second threshold and equal to or greater than the first threshold can include, for example, a case where the received specific wireless signal has great jitter.

By the way, in the present embodiment, a wireless signal which changes at a timing which is the same or substantially the same as the setting of the symbol rate, that is, a wireless signal for which temporal positions of signal change points within one cycle defined by the setting of the symbol rate are the same or substantially the same among the plurality of signal change points is judged as the specific wireless signal. Thus, the symbol rate of the wireless signal which is judged by the judging unit 65 as the specific wireless signal is basically the same or substantially the same as the symbol rate in the setting of the symbol rate. However, also in a case of a wireless signal having a symbol rate which is 1/N times (where N is an integer of 2 or greater) of the symbol rate in the setting of the symbol rate, temporal positions of signal change points within one cycle defined by the setting of the symbol rate are the same among the plurality of signal change points. Consequently, the symbol rate is preferably set so as to match the symbol rate of the specific wireless signal to be received, that is, the symbol rate of the wireless signal transmitted by the wireless communication unit 113 of the capsule endo scope 101.

(Operation of Image Acquiring Unit, Display Control Unit and Storage Unit)

Operation of the image acquiring unit 7, the display control unit 8 and the storage unit 4 will be described next with reference to FIG. 3 and FIG. 4. The operation of the image acquiring unit 7 will be described first. The image acquiring unit 7 receives input of the wireless signal restored by the demodulating unit 5, the detection result of the signal detecting unit 6, that is, the judgment result of the judging unit 65. The image acquiring unit 7 then acquires image data from the wireless signal which is judged as the specific wireless signal by the judging unit 65. Further, the image acquiring unit 7 outputs the acquired image data to the storage unit 4 and the display control unit 8.

The operation of the display control unit 8 will be described next. The display control unit 8 receives input of the detection result of the signal detecting unit 6, that is, the judgment result of the judging unit 65, and the image data acquired by the image acquiring unit 7. The display control unit 8 causes information corresponding to the judgment result as to whether the reception condition is good or bad among the judgment result of the judging unit 65 and an image corresponding to the image data to be displayed at the display unit 10. The above-described information and image are, for example, displayed on one screen of the display unit 10 at the same time by the display control unit 8. The above-described information may be expressed with a number or a predetermined index which changes in accordance with the judgment result as to whether the reception condition is good or bad and the parameter used in the judgment (parameters calculated by the calculating unit 64). Examples of the predetermined index can include, for example, a mark such as ○ and ×, color, and a pictogram such as a graph.

Further, the display control unit 8 may cause images corresponding to all image data to be displayed at the display unit 10 or may select content to be outputted to the display unit 10 based on the judgment result as to whether the reception condition is good or bad. In the latter case, the display control unit 8 may cause only images corresponding to image data of the wireless signal for which it is judged that the reception condition is good to be displayed at the display unit 10. In this case, images corresponding to image data of the wireless signal for which it is judged that the reception condition is bad are not displayed at the display unit 10.

The operation of the storage unit 4 will be described next. The storage unit 4 receives input of the detection result of the signal detecting unit 6, that is, the judgment result of the judging unit 65, and the image data acquired by the image acquiring unit 7. The storage unit 4 stores information corresponding to the judgment result as to whether the reception condition is good or bad among the judgment result of the judging unit 65 and the image data in association with each other.

Note that the storage unit 4 may store all image data or may select content to be stored based on the judgement result as to whether the reception condition is good or bad. In the latter case, the storage unit 4 may store only image data of the wireless signal for which it is judged that the reception condition is good. In this case, image data of the wireless signal for which it is judged that the reception condition is bad is discarded.

(Action and Effects)

Action and effects of the wireless communication apparatus 1 and the capsule endoscope system 100 according to the present embodiment will be described next. In the present embodiment, whether or not the received wireless signal is a wireless signal transmitted by the wireless communication unit 113 of the capsule endoscope 101 (hereinafter, also referred to as a transmission signal) can be judged through a series of processing at the phase detecting unit 61, the vector generating unit 62, the vector synthesizing unit 63, the calculating unit 64 and the judging unit 65. In the above-described series of processing, signal change points of the wireless signal are detected as phases, vectors corresponding to the phases are generated, a synthesized vector is generated by synthesizing a plurality of vectors, and a parameter having a correspondence relationship with a magnitude of the generated synthesized vector is calculated. Computation used in these series of processing is simple compared to computation in DFT and FFT. Consequently, according to the present embodiment, it is possible to make a circuit scale smaller than a circuit scale in a case where frequency components of the wireless signal are detected by utilizing DFT and FFT. From the above, according to the present embodiment, it is possible to specify a transmission signal without making a circuit scale larger.

Note that typically, it is necessary to cause a circuit which detects frequency components of a wireless signal received by utilizing DFT and FFT to operate at a relatively fast operation clock which is an integral multiple of a symbol rate of a wireless signal to be received. In contrast, in the present embodiment, it is not necessary to fulfill the above-described requirements. Consequently, in the present embodiment, it is possible to set a relatively slow operation clock.

Further, in the present embodiment, the judging unit 65 judges whether the reception condition of the specific wireless signal is good or bad by comparing the parameter with the predetermined threshold. By this means, according to the present embodiment, it is possible to notify a user of the reception condition and, as described above, it is possible to control content to be displayed at the display unit 10 and content to be stored in the storage unit 4 based on the judgement result as to whether the reception condition is good or bad. Particularly, in a case where the content to be stored in the storage unit 4 is controlled based on the judgment result as to whether the reception condition is good or bad, it is possible to reduce an amount of data to be stored in the storage unit 4 by discarding image data of a wireless signal for which it is judged that the reception condition is bad.

Further, the capsule endoscope 101 intermittently transmits a wireless signal to reduce power consumption. The parameter to be calculated by the calculating unit 64 becomes equal to or greater than a predetermined threshold while the capsule endoscope 101 transmits a wireless signal, and the parameter becomes less than the predetermined threshold while the capsule endoscope 101 does not transmit a wireless signal.

Figure 12:
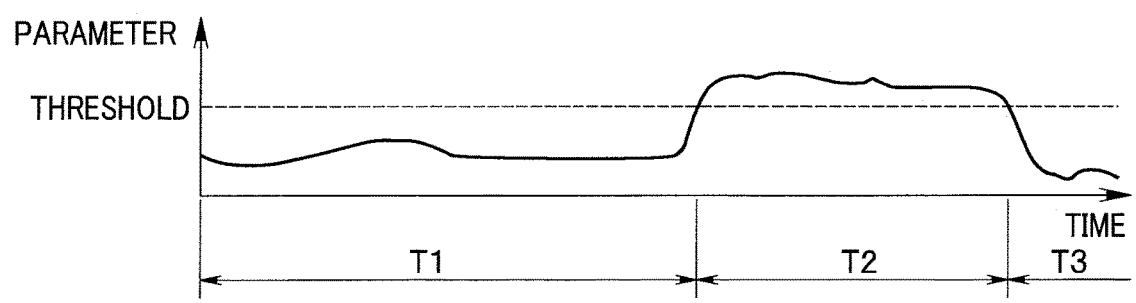
FIG. 12 is an explanatory diagram schematically illustrating change of a parameter in the first embodiment of the present invention.

FIG. 12 is an explanatory diagram schematically illustrating change of the parameter to be calculated by the calculating unit 64. In FIG. 12, a period T2 is a period during which a magnitude of the parameter is equal to or greater than the predetermined threshold, and is a period during which the capsule endoscope 101 transmits a wireless signal. Periods T1 and T3 before and after the period T2 are periods during which the magnitude of the parameter is less than the predetermined threshold, and are periods during which the capsule endoscope 101 does not transmit a wireless signal. According to the present embodiment, it is possible to specify whether or not the period is a period during which the capsule endoscope 101 transmits a wireless signal based on the parameter.

Note that during a period while the capsule endoscope 101 does not transmit a wireless signal, it is possible to temporarily stop operation of at least one of the storage unit 4, the image acquiring unit 7 and the display control unit 8. By this means, according to the present embodiment, it is possible to reduce power consumption of the wireless communication apparatus 1.

Further, in the present embodiment, the synthesized vector is generated by synthesizing a plurality of vectors generated based on a plurality of signal change points detected during a predetermined period. To improve judgment accuracy at the judging unit 65, a period which is long to some extent, such as a period corresponding to a plurality of cycles defined by the setting of the symbol rate is preferably set as the predetermined period. Note that whether or not the wireless signal is the specific wireless signal is judged at a preamble located at a head portion of the wireless signal. It is therefore necessary to set the predetermined period which has a length falling within a period of the preamble.

Figure 13:
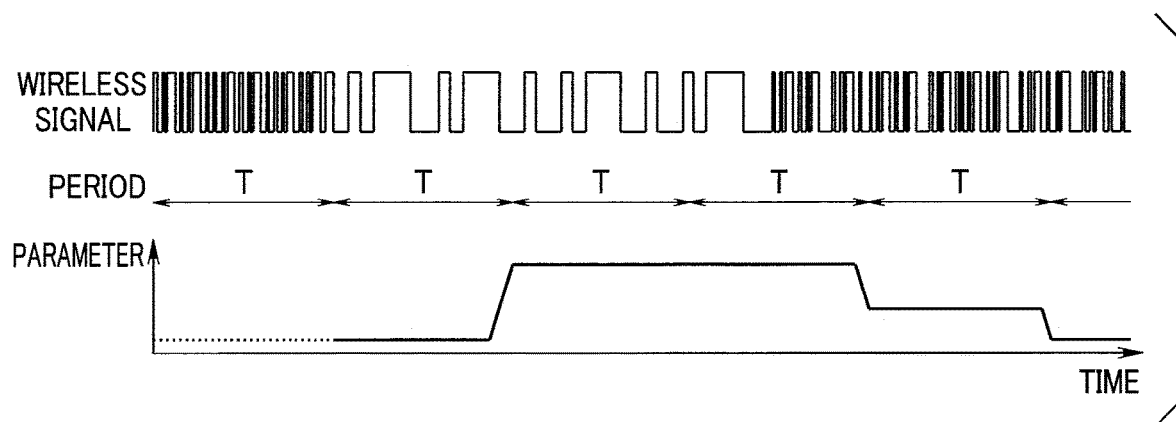
FIG. 13 is an explanatory diagram illustrating a first example of detection periods of signal change points in the first embodiment of the present invention.
Figure 14:
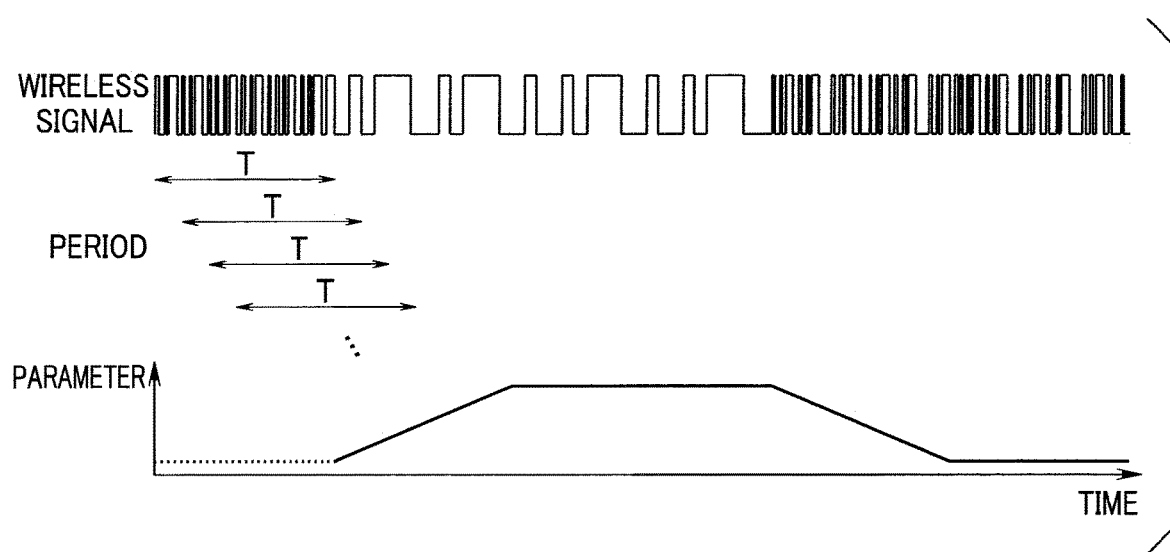
FIG. 14 is an explanatory diagram illustrating a second example of the detection periods of the signal change points in the first embodiment of the present invention.

Further, in the present embodiment, a plurality of periods are set as the predetermined period during which signal change points are to be detected, and the synthesized vectors are sequentially generated. In other words, a plurality of synthesized vectors are generated over a plurality of periods. The respective plurality of periods may overlap with each other or do not have to overlap with each other. FIG. 13 is a schematic diagram illustrating a first example of detection periods of the signal change points. FIG. 14 is a schematic diagram illustrating a second example of the detection periods of the signal change points. FIG. 13 and FIG. 14 indicate an example of the wireless signal and change of the parameter calculated based on this wireless signal. Further, FIG. 13 and FIG. 14 indicate predetermined periods during which the signal change points are to be detected with arrows with a symbol T. FIG. 13 illustrates an example where the plurality of periods T do not overlap with each other. FIG. 14 illustrates an example where the plurality of periods T overlap with each other.

In the example illustrated in FIG. 13, the number of synthesized vectors to be generated decreases compared to the example illustrated in FIG. 14, so that it is possible to reduce an amount of a series of processing at the phase detecting unit 61, the vector generating unit 62, the vector synthesizing unit 63, the calculating unit 64 and the judging unit 65. In contrast, in the example illustrated in FIG. 14, while the amount of the above-described series of processing increases, it is possible to recognize a transient state from when the capsule endoscope 101 starts transmission of a wireless signal until when the parameter changes, so that it is possible to reduce signals which are used only to specify a transmission signal.

Note that in the present embodiment, the setting of the symbol rate is fixed at a predetermined value. However, the setting of the symbol rate may be, for example, changed over time.

Second Embodiment

A second embodiment of the present invention will be described next. A configuration of the wireless communication apparatus 1 according to the present embodiment is different from the configuration of the wireless communication apparatus 1 in the first embodiment in the following points. In the present embodiment, a signal detecting unit 106 is provided in place of the signal detecting unit 6 in the first embodiment. The signal detecting unit 106 is configured to be able to detect predetermined information from a wireless signal received by the wireless communication apparatus 1 and output the detection result to the storage unit 4, the image acquiring unit 7 and the display control unit 8 (see FIG. 3).

Figure 15:
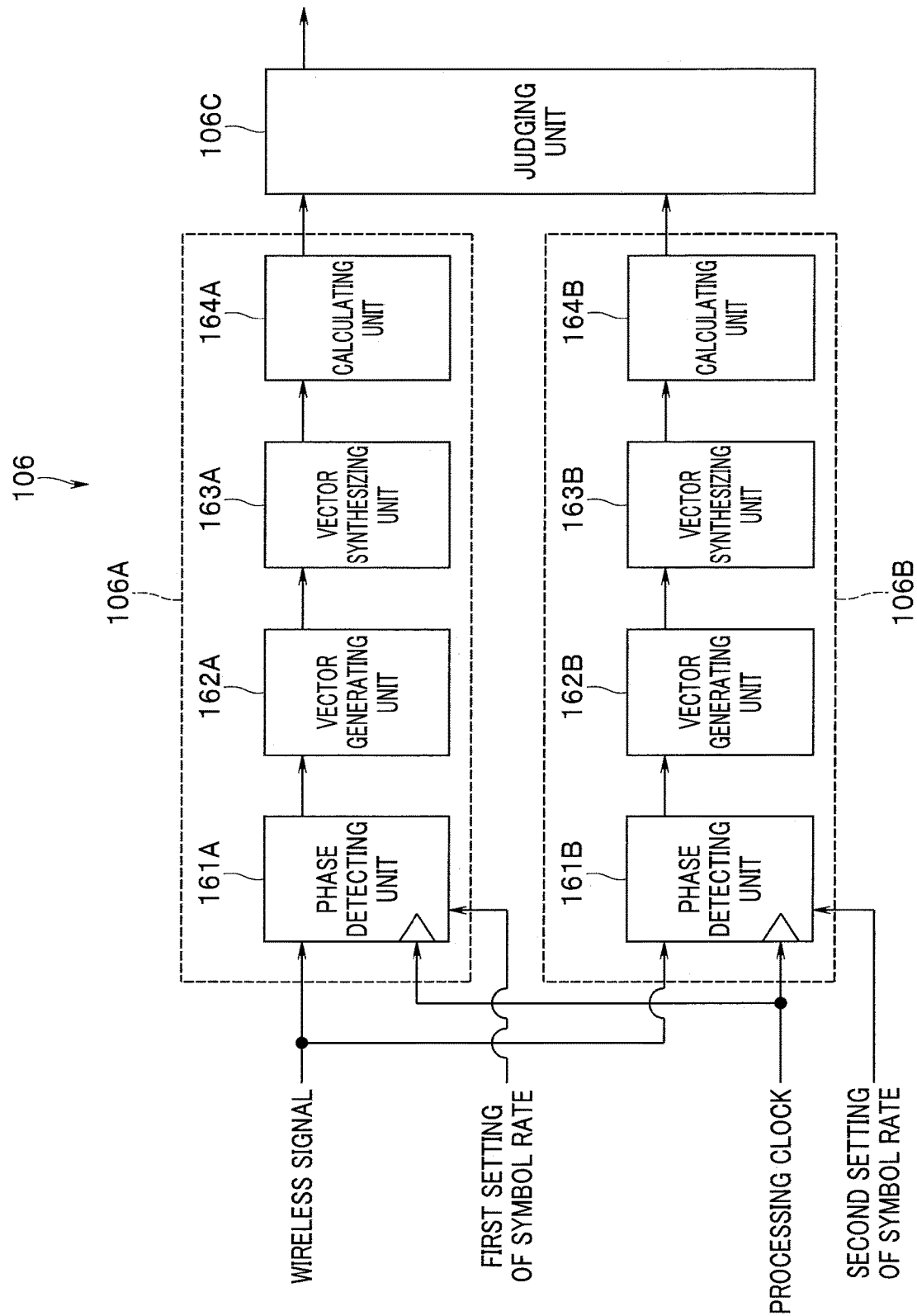
FIG. 15 is a functional block diagram illustrating a configuration of a signal detecting unit in a second embodiment of the present invention.

A configuration of the signal detecting unit 106 will be described below with reference to FIG. 15. FIG. 15 is a functional block diagram illustrating the configuration of the signal detecting unit 106. As illustrated in FIG. 15, the signal detecting unit 106 includes a plurality of computing units 106A and 106B and one judging unit 106C. The plurality of computing units 106A and 106B are provided in parallel on a side closer to the demodulating unit 5 (see FIG. 3). The judging unit 106C is provided downstream the plurality of computing units 106A and 106B.

The computing unit 106A includes a phase detecting unit 161A, a vector generating unit 162A, a vector synthesizing unit 163A and a calculating unit 164A provided from a side closer to the demodulating unit 5 (see FIG. 3). Functions of the phase detecting unit 161A, the vector generating unit 162A, the vector synthesizing unit 163A and the calculating unit 164A are basically the same as the functions of the phase detecting unit 61, the vector generating unit 62, the vector synthesizing unit 63 and the calculating unit 64 in the first embodiment.

The computing unit 106B includes a phase detecting unit 161B, a vector generating unit 162B, a vector synthesizing unit 163B and a calculating unit 164B provided from a side closer to the demodulating unit 5 (see FIG. 3). Functions of the phase detecting unit 161B, the vector generating unit 162B, the vector synthesizing unit 163B and the calculating unit 164B are basically the same as the functions of the phase detecting unit 61, the vector generating unit 62, the vector synthesizing unit 63 and the calculating unit 64 in the first embodiment.

The phase detecting units 161A and 161B are respectively configured to be able to read out setting of the symbol rate stored in the storage unit 4 (see FIG. 3). In the present embodiment, the setting of the symbol rate is different for each of the plurality of computing units 106A and 106B. In other words, in the present embodiment, the setting of the symbol rate read out by the phase detecting unit 161A is different from the setting of the symbol rate read out by the phase detecting unit 161B. Hereinafter, the setting of the symbol rate read out by the phase detecting unit 161A will be referred to as first setting of the symbol rate, and the setting of the symbol rate read out by the phase detecting unit 161B will be referred to as second setting of the symbol rate.

The judging unit 106C receives input of the parameter calculated by the calculating unit 164A (hereinafter, referred to as a first parameter) and the parameter calculated by the calculating unit 164B (hereinafter, referred to as a second parameter). The judging unit 106C judges the symbol rate of the received wireless signal based on the first and the second parameters. This judgment is performed using a predetermined threshold. In other words, the judging unit 106C judges the symbol rate of the wireless signal by comparing each of the first and the second parameters with the predetermined threshold.

For example, in a case where the first parameter is equal to or greater than the predetermined threshold, and the second parameter is less than the predetermined threshold, it is judged that the received wireless signal is a wireless signal having a symbol rate which is the same as the first setting of the symbol rate. Further, in a case where the second parameter is equal to or greater than the predetermined threshold, and the first parameter is less than the predetermined threshold, it is judged that the received wireless signal is a wireless signal having a symbol rate which is the same as the second setting of the symbol rate. Further, in a case where both of the first parameter and the second parameter are equal to or greater than the predetermined threshold, it is judged that the received wireless signal is a wireless signal having a symbol rate which is the same as the symbol rate having a smaller value, that is, slower, out of the first setting of the symbol rate and the second setting of the symbol rate.

Further, in a case where both of the first parameter and the second parameter are less than the predetermined threshold, it is judged that the received wireless signal is noise.

Action and effects which are peculiar to the present embodiment will be described next. At the capsule endoscope 101 (see FIG. 1), there is a case where the symbol rate is changed in accordance with a state of a communication environment and a data amount of image data. In contrast, in the present embodiment, a plurality of computing units 106A and 106B for which the setting of symbol rate is different are provided. By this means, according to the present embodiment, even in a case where the symbol rate of the wireless signal is changed, it is possible to judge whether or not the received wireless signal is the wireless signal transmitted from the wireless communication unit 113 of the capsule endoscope 101 by judging the symbol rate of the wireless signal.

Note that in a similar manner to the first embodiment, also in a case of a wireless signal having a symbol rate which is 1/N times (where N is an integer of 2 or greater) of the first setting of the symbol rate, temporal positions of signal change points within one cycle defined by the first setting of the symbol rate are the same among the plurality of signal change points. Consequently, the first setting of the symbol rate is preferably made the same as a symbol rate of the wireless signal to be received, that is, a symbol rate of the wireless signal to be transmitted by the wireless communication unit 113 of the capsule endoscope 101. In a similar manner, also in a case of a wireless signal having a symbol rate which is 1/N times of the second setting of the symbol rate, temporal positions of signal change points within one cycle defined by the second setting of the symbol rate are the same among the plurality of signal change points. Consequently, the second setting of the symbol rate is preferably made the same as a symbol rate of the wireless signal to be received, that is, a symbol rate of the wireless signal to be transmitted by the wireless communication unit 113 of the capsule endoscope 101, which is different from the first setting of the symbol rate.

Further, in the present embodiment, an example of a case where there are two computing units has been described. However, the number of the plurality of computing units is not limited to two, and there may be three or more computing units. By this means, even in a case where the capsule endoscope 101 changes the symbol rate in three or more patterns, it is possible to judge whether the received wireless signal is the wireless signal transmitted by the wireless communication unit 113 of the capsule endoscope 101.

Other configurations, action and effects of the present embodiment are similar to the configurations, action and effects in the first embodiment.

Third Embodiment

Figure 16:
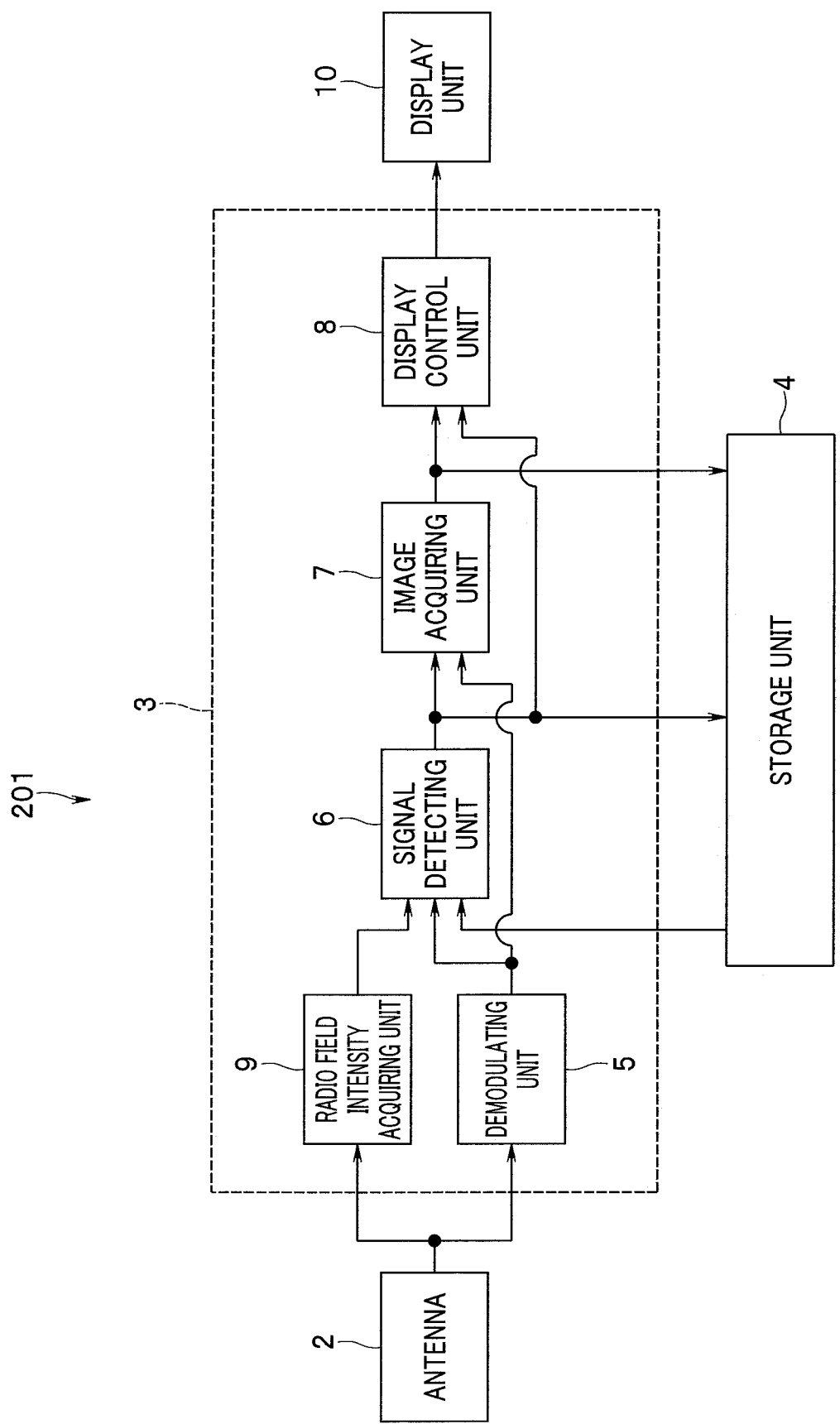
FIG. 16 is a functional block diagram illustrating a configuration of a wireless communication apparatus according to a third embodiment of the present invention.
Figure 17:
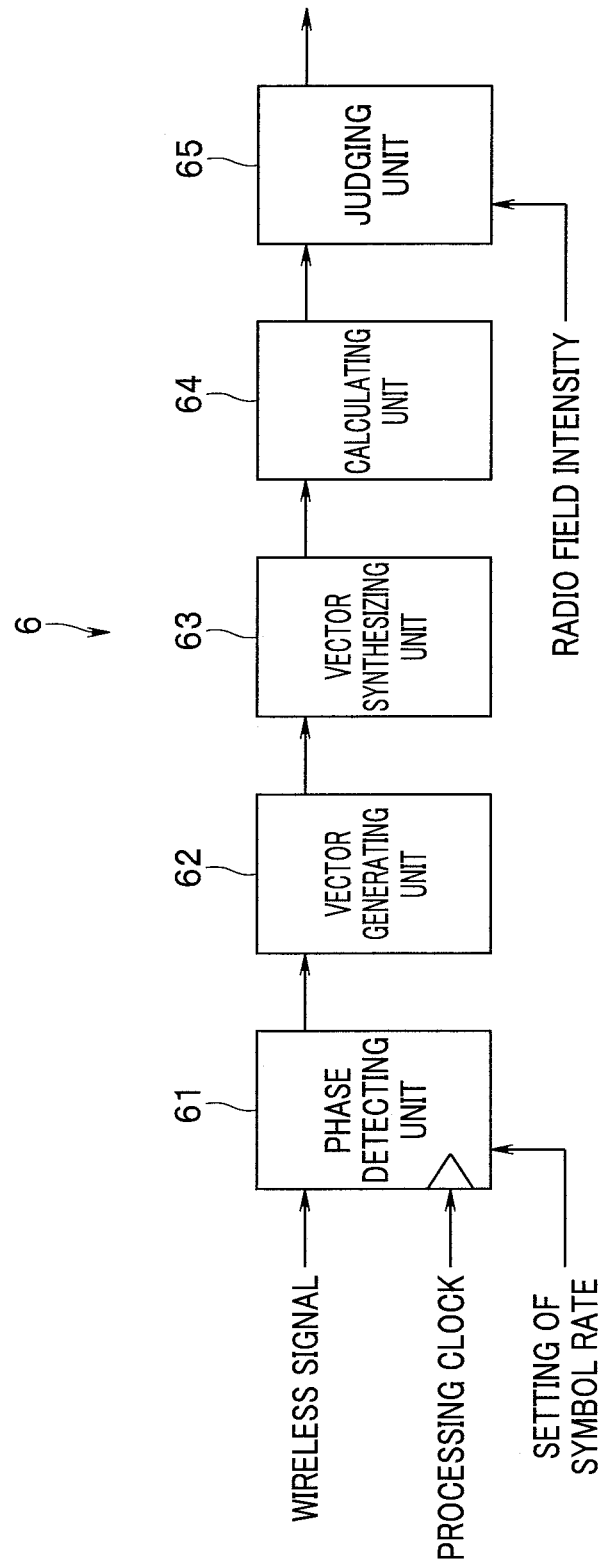
FIG. 17 is a functional block diagram illustrating a configuration of a signal detecting unit in the third embodiment of the present invention.

A third embodiment of the present invention will be described next with reference to FIG. 16 and FIG. 17. FIG. 16 is a functional block diagram illustrating a configuration of a wireless communication apparatus according to the present embodiment. FIG. 17 is a functional block diagram illustrating a configuration of a signal detecting unit in the present embodiment. In a similar manner to the first embodiment, the signal processing unit 3 includes the demodulating unit 5, the signal detecting unit 6, the image acquiring unit 7 and the display control unit 8. As illustrated in FIG. 17, the configuration of the signal detecting unit 6 is basically similar to the configuration in the first embodiment.

In the present embodiment, the signal processing unit 3 further includes a radio field intensity acquiring unit 9. The radio field intensity acquiring unit 9 acquires radio field intensity of the wireless signal from the wireless signal received by the antenna 2, and outputs information of the radio field intensity to the judging unit 65 of the signal detecting unit 6. The radio field intensity is, for example, expressed with a magnitude of received power.

As illustrated in FIG. 17, the judging unit 65 receives input of information of the radio field intensity. In the present embodiment, the judging unit 65 judges whether the reception condition of the specific wireless signal is good or bad based on the information of the radio field intensity acquired by the radio field intensity acquiring unit 9. The judging unit 65 judges whether the reception condition is good or bad by comparing the magnitude of the radio field intensity with a predetermined threshold (hereinafter, referred to as a third threshold). Here, in a similar manner to the first embodiment, a threshold to be used by the judging unit 65 to judge whether or not the wireless signal is the specific wireless signal is set as the first threshold. The judging unit 65 judges whether or not the wireless signal is the specific wireless signal by comparing the parameter calculated by the calculating unit 64 with the first threshold. In a case where the parameter is less than the first threshold, the judging unit 65 judges that the received wireless signal is not the specific wireless signal.

In a case where the parameter is equal to or greater than the first threshold, the judging unit 65 judges that the received wireless signal is the specific wireless signal. In this case, the judging unit 65 then judges whether the reception condition is good or bad by comparing the magnitude of the radio field intensity with the third threshold. In a case where the magnitude of the radio field intensity is equal to or greater than the third threshold, the judging unit 65 judges that the reception condition is good. On the other hand, in a case where the magnitude of the radio field intensity is less than the third threshold, the judging unit 65 judges that the reception condition is bad. Note that in the above-described judgment, for example, information of the radio field intensity of the wireless signal which has been received immediately before the judgment is used.

Other configurations, action and effects in the present embodiment are similar to the configurations, action and effects in the first embodiment.

The present invention is not limited to the above-described embodiments, and various changes, modifications, and the like, can be made within a scope not deviating from the gist of the present invention. For example, the radio field intensity acquiring unit 9 in the third embodiment may be provided at the wireless communication apparatus 1 according to the second embodiment. In this case, the radio field intensity acquiring unit 9 outputs the information of the radio field intensity to the judging unit 106C of the signal detecting unit 106.

Further, the wireless communication apparatus of the present invention may specify a wireless signal transmitted by a specific wireless transmission apparatus among a plurality of wireless signals transmitted by a plurality of wireless transmission apparatuses.

What is claimed is:

1. A wireless communication apparatus comprising a processor,
    the processor being configured to
    detect a signal change point at which a signal decoded from a received wireless signal changes, and detect a temporal position of the signal change point within one cycle defined by a predetermined symbol rate as a phase,
    generate a vector which corresponds to the phase and which has a predetermined magnitude,
    synthesize the vector in plurality to generate a synthesized vector,
    calculate a parameter having a correspondence relationship with a magnitude of the synthesized vector, and
    judge whether or not the received wireless signal is a wireless signal from a predetermined transmission apparatus based on the parameter.

2. The wireless communication apparatus according to claim 1,
    wherein the synthesized vector is generated by synthesizing the vector in plurality generated based on the signal change point in plurality detected during a predetermined period.

3. The wireless communication apparatus according to claim 1,
    wherein the processor judges whether the received wireless signal is the wireless signal from the predetermined transmission apparatus or noise by comparing the parameter with a predetermined threshold.

4. The wireless communication apparatus according to claim 1,
    wherein the processor judges whether a reception condition of the wireless signal from the predetermined transmission apparatus is good or bad by comparing the parameter with a predetermined threshold.

5. The wireless communication apparatus according to claim 4,
    wherein the processor is further configured to cause information corresponding to a judgment result as to whether the reception condition of the wireless signal from the predetermined transmission apparatus is good or bad, to be displayed at a display apparatus.

6. The wireless communication apparatus according to claim 4,
    wherein the wireless signal from the predetermined transmission apparatus includes image data,
    the processor is further configured to acquire the image data from the wireless signal from the predetermined transmission apparatus, and cause information corresponding to a judgment result as to whether the reception condition of the wireless signal from the predetermined transmission apparatus is good or bad and an image corresponding to the image data to be displayed at a display apparatus, and
    the wireless communication apparatus further comprises a memory which stores the judgment result and the image data in association with each other.

7. The wireless communication apparatus according to claim 4,
    wherein the wireless signal from the predetermined transmission apparatus includes image data,
    the processor is further configured to acquire the image data from the wireless signal from the predetermined transmission apparatus, and
    the wireless communication apparatus further comprises a memory which stores only the image data of the wireless signal from the predetermined transmission apparatus for which it is judged that a reception condition is good.

8. The wireless communication apparatus according to claim 4,
    wherein the wireless signal from the predetermined transmission apparatus includes image data, and
    the processor is further configured to acquire the image data from the wireless signal from the predetermined transmission apparatus and cause only an image corresponding to the image data of the wireless signal from the predetermined transmission apparatus for which it is judged that a reception condition is good to be displayed at a display apparatus.

9. A wireless communication apparatus comprising a processor configured to perform a plurality of kinds of computation processing,
    the processor being configured to, for each of the plurality of kinds of computation processing:

detect a signal change point at which a signal decoded from a received wireless signal changes and detect a temporal position of the signal change point within one cycle defined by a predetermined symbol rate as a phase;

generate a vector which corresponds to the phase and which has a predetermined magnitude;

synthesize the vector in plurality to generate a synthesized vector; and calculate a parameter having a correspondence relationship with a magnitude of the synthesized vector, wherein the symbol rate is different for each of the plurality of kinds of computation processing, and the processor is further configured to judge a symbol rate of the wireless signal based on the parameter in plurality calculated through the plurality of kinds of computation processing.

10. The wireless communication apparatus according to claim 9, wherein the processor judges the symbol rate of the wireless signal by comparing each of the parameter in plurality with a predetermined threshold.

11. A capsule endoscope system comprising:

a capsule endoscope configured to pick up an image inside a subject to generate image data and transmit the image data using a wireless signal; and the wireless communication apparatus according to claim 1.

12. A judgment method comprising:

detecting a signal change point at which a signal decoded from a received wireless signal changes and detecting a temporal position of the signal change point within one cycle defined by a predetermined symbol rate as a phase;

generating a vector which corresponds to the phase and which has a predetermined magnitude;

synthesizing the vector in plurality to generate a synthesized vector;

calculating a parameter having a correspondence relationship with a magnitude of the synthesized vector; and judging whether or not the received wireless signal is a wireless signal from a predetermined transmission apparatus based on the parameter.

* * * * *